United States Patent [19]

Lin et al.

[11] Patent Number: 5,136,084

[45] Date of Patent: Aug. 4, 1992

[54] PROCESS FOR THE ACETYLATION OF A MONO-SUBSTITUTED PHENOL OR A MONO-SUBSTITUTED NAPHTHOL

[75] Inventors: Shu-Chung Lin; Min-Hon Rei, both of Taipei, Taiwan

[73] Assignee: San Fu Chemical Co., Ltd., Taipei, Taiwan

[21] Appl. No.: 714,910

[22] Filed: Jun. 14, 1991

Related U.S. Application Data

[63] Continuation-in-part of Ser. No. 426,326, Oct. 24, 1989, abandoned.

[51] Int. Cl.$^5$ ............................................. C07C 67/03
[52] U.S. Cl. ................................. 560/139; 560/130; 560/143; 560/144
[58] Field of Search ................ 560/130, 139, 143, 144

[56] References Cited

U.S. PATENT DOCUMENTS 4,665,215  5/1987  Davenport .................... 560/130
4,927,956  5/1990  Vicari et al. .................. 560/130

Primary Examiner—Jose G. Dees
Assistant Examiner—Vera C. Clarke
Attorney, Agent, or Firm—Ladas & Parry

[57] ABSTRACT

A novel process for the acetylation of a mono-substituted phenol or a mono-substituted naphthol is disclosed which comprises reacting the said mono-substituted phenol or the said mono-substituted naphthol respectively with vinyl acetate at a temperature of not more than 160° C.

7 Claims, 1 Drawing Sheet

PROCESS FOR THE ACETYLATION OF A MONO-SUBSTITUTED PHENOL OR A MONO-SUBSTITUTED NAPHTHOL

This application is a continuation-in-part of application Ser. No. 07/426,326 filed on Oct. 24, 1989, now abandoned.

BACKGROUND OF THE INVENTION

1. Field of the Invention

This invention relates to a novel process for the acetylation of a mono-substituted phenol and a mono-substituted naphthol which comprises reacting respectively a mono-substituted phenol and a mono-substituted naphthol with an acetylating agent vinyl acetate at a low temperature. The substituent in the mono-substituted phenol referred to above is selected from the group consisting of halo, hydroxy and carboxy at o-, m-, or p-position with respect to the hydroxy group of the phenol, while the mono-substituted naphthol referred to above is 2-hydroxy-6-naphthoic acid.

The acetylated final product, for example, p-acetoxybenzoic acid finds its use as a monomer in the production of liquid-crystal polymers such as "Vectra" and "X7G", etc. Such polymers provide high heat resistance, tensile strength and dimensional stability, which improve the qualities of Engineering Plastics among different fields.

2. Brief Description of the Prior Art

Traditionally p-acetoxybenzoic acid is prepared by acetylation with more expensive acetic anhydride, under more drastic reaction condition. References relating to the preparation and application of p-acetoxybenzoic acid copolymers are cited in following literature:

U.S. Pat. Nos. 4,083,839; 4,161,470; 4,219,461; 4,264,802; 4,267,289; 4,279,803; 4,299,756; 4,318,841; 4,355,132; 4,355,133; 4,355,134; 4,429,100; 4,473,682; 4,522,974 Other acetylated final product, such as phenyl acetate finds its use as an organic solvent or intermediate for various organic syntheses. The advantages of using vinyl acetate instead of the traditional acetic acid, acetic anhydride or acetyl chloride as the acetylating agent are as follows:

(1) the reaction is carried out at a temperature lower than 100° C.;

(2) the reaction by-product can be easily separated under the reaction condition; and (3) due to a lower reaction temperature and a less acidic environment a less expensive construction material may be used for the reaction system.

Acetylation of phenolic compounds and naphtholic compounds is usually more difficult than that of aliphatic compounds because of more the acidic nature of the phenolic hydroxy group and the naphtholic hydroxyl group. As a result, the reaction usually requires a higher temperature and a stronger acidic condition, and the product isolation is more difficult due to a more complicated reaction mixture. Therefore, a higher cost of production is usually required.

Acetic anhydride and acetyl chloride are two common acetylating agents used in the industry. Both are sensitive to hydrolysis, and water has to be carefully removed during the course of the reaction. During the reaction the former yields one equivalent of acetic acid, and the latter gives one equivalent of hydrogen chloride. Recovery of acetic acid needs an expensive distillation step. Hydrogen chloride may cause severe corrosion problems for the production equipment and may result in an extra load for waste water treatment.

SUMMARY OF THE INVENTION

This invention demonstrates the use of vinylacetate as an alternate acetylating agent. The reaction by-product is acetaldehyde, which can be easily evaporated and does not cause corrosion problems. Recovered acetaldehyde may be used to synthesize useful organic compounds such as pentaerythritol or ethylacetate. Vinyl acetate has been used in the acetylation of starch (U.S. Pat. Nos. 3,022,289; 3,081,296; 4,038,482; 2,731,492). However, the use of vinylacetate as an acetylating agent for the phenolic compounds and naphtholic compound has not been heretofore observed.

DETAILED DESCRIPTION OF THE PREFERRED EMBODIMENT

Figure 1:
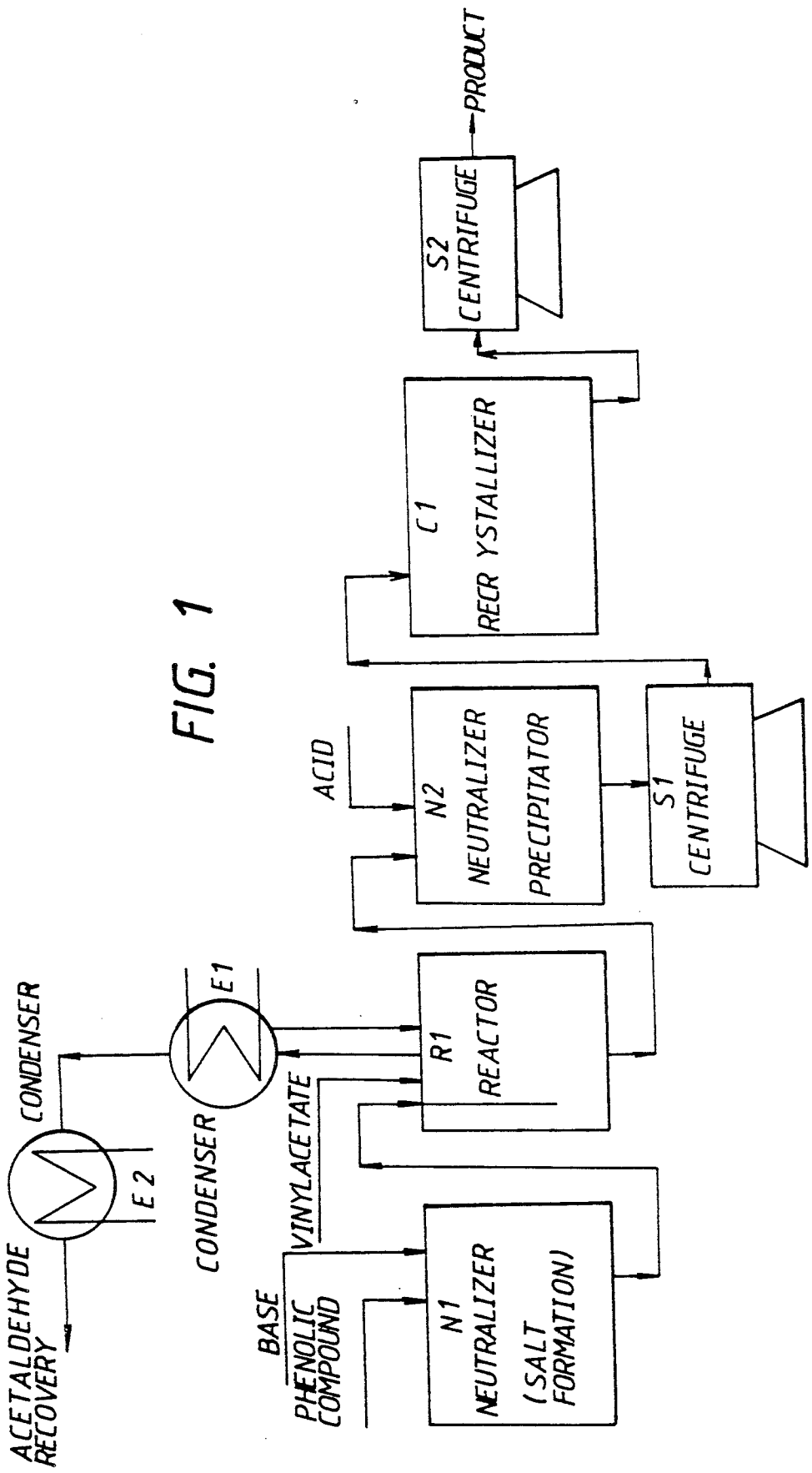
FIG. 1 is a functional block diagram of the steps in the process scheme for the acetylation of mono-substituted phenols or mono-substituted naphthols by vinyl acetate in accordance with the present invention.

In order to increase the nucleophilicity of the hydroxy group, the mono-substituted phenol and mono-substituted naphthol are respectivity first treated with a base. As a result the mono-substituted phenol and mono-substituted naphthol may be easily acetylated by vinyl acetate in an amount of from about 1 to 10 mole ratio based on the mono-substituted phenol or mono-substituted naphthol at a temperature of not more than 160° C., preferably from 20° C. to 70° C. at a pressure of from about 1 to 10 atmospheres, preferably from 1 to 3 atmospheres. Many inorganic bases such as the hydroxide or the carbonate of lithium, sodium, potassium and rubidium, or organic amine and ammonium hydroxide may be used in an amount of from 0.05 to 2.5 mole per mole of the mono-substituted phenol and mono-substituted naphthol. Any organic solvent which is capable of dissolving the salt of mono-substituted phenol or mono-substituted naphthol formed by the reaction of mono-substituted phenol or mono-substituted naphthol can be used.

Para-hydroxybenzoic acid is used as substrate in this invention to demonstrate the acetylation capability of vinyl acetate. In example 1, the acetylation selectivity of vinyl acetate is found to be superior to that of acetic anhydride, resulting in a simpler reaction mixture.

In examples 2, 3, 4 and 5, the effects of vinyl acetate usage, bases and their usages, and the water content on the acetylation reaction are discussed. In example 6, various solvents are employed to study their effects on the reaction. Finally, in example 7, various mono-substituted phenols and mono-substituted naphthol are tested, and except phenol, satisfactory results have been obtained.

A simplified process scheme for the acetylation of mono-substituted phenols by vinyl acetate is shown in FIG. 1. The base-treated phenol or naphthol compound (Ar-O-M) from neutralizer N1 is charged into a well-stirred reactor R1, and heated to the reaction temperature (0°–150° C.). After charging vinyl acetate, reactor R1 is then pressurized to a desired pressure (1–10 atm). The vapor is partially condensed by condenser E1 and refluxed back to the reactor R1; the by-product acetaldehyde is received through condenser E2. After reaction, the mixture is acidified in the neutralization tank N2, and the precipitated solids separated by a centrifuge S1. Recrystallization of the solid at recrystallizer C1 is then employed to yield the high purity product which is separated by a centrifuge S2. In order to avoid hydrolysis of vinyl acetate at high temperatures, the acetylation may also be carried out by a reverse addition method, e.g., by adding the base-treated mono-substituted phenol or naphthol slowly into the stirred vessel containing vinyl acetate.

EXAMPLE 1

Vinyl Acetate vs. Acetic Anhydride

Para-hydroxybenzoic acid was acetylated by vinyl acetate and acetic anhydride respectively. The reaction conditions were as follows:

VINYL ACETATE: 100 grams of para-hydroxybenzoic acid and 81 grams of potassium hydroxide were mixed into 400 mls of water in a stirred vessel. 80 mls of vinyl acetate was added and reacted at 28° C. for 2 hours.

ACETIC ANHYDRIDE: 100 grams of para-hydroxybenzoic acid, 120 mls of acetic acid and 120 mls of acetic anhydride were stirred and reacted at 125°-130° C. for 2 hours.

RESULTS: (as shown in Table 1)

TABLE 1

| REAGENT | CONVERSION OF PARA-HYDROXYBENZOIC ACID (%) | SELECTIVITY (%) |
|---|---|---|
| VINYL ACETATE | 70 | 100 |
| ACETIC ANHYDRIDE | 99 | 78 |

EXAMPLE 2

Effect of Vinyl Acetate Usage 400 ml aqueous solution containing 100 grams of para-hydroxybenzoic acid and 81 grams of potassium hydroxide was reacted with various amount of vinyl acetate at 28° C. for 2 hours. The results are shown in Table 2.

TABLE 2

| VINYLACETATE/PARA-HYDROXYBENZOIC ACID (MOLAR RATIO) | CONVERION OF PARA-HYDROXYBENZOIC ACID (%) |
|---|---|
| 1.6 | 61 |
| 3.0 | 72 |
| 5.0 | 74 |

EXAMPLE 3

Effect of the Amount of Base

Potassium hydroxide was added to 100 grams of para-hydroxybenzoic acid in 400 mls of water. After the addition of 200 mls of vinylacetate the mixture was reacted at 28° C. for 2 hours. Table 3 shows the effect of the quantity of base on the conversion.

TABLE 3

| KOH/PARA-HYDROXYBENZOIC ACID (MOLAR RATIO) | CONVERSION OF PARA-HYDROXYBENZOIC ACID (%) |
|---|---|
| 1.2 | 64 |
| 1.5 | 79 |
| 2.0 | 72 |
| 2.5 | 65 |

EXAMPLES

Effect of Different Bases

Under the same operating conditions as example 1 the effect of the various bases are shown in Table 4.

TABLE 4

| BASE | BASE/PARA-HYDROXYBENZOIC ACID (MOLAR RATIO) | CONVERSION OF PARA-HYDROXYBENZOIC ACID (%) |
|---|---|---|
| SODIUM HYDROXIDE | 1.4 | 71 |
| POTASSIUM HYDROXIDE | 1.5 | 70 |
| LITHIUM HYDROXIDE | 2.0 | 64 |
| SODIUM CARBONATE | 0.85 | 69 |
| POTASSIUM CARBONATE | 0.8 | 70 |
| BARIUM HYDROXIDE | 1.2 | 30 |
| TRIETHYL AMINE | 1.2 | 30 |
| AMMONIUM HYDROXIDE | 1.46 | 6 |

EXAMPLE 5

Effect of Water Content 100 grams of para-hydroxybenzoic acid was first treated with an aqueous solution containing 81 grams of potassium hydroxide and various amount of water. 200 mls of vinyl acetate was then mixed in at 28° C. and reacted for 2 hours. Table 5 shows the effect of water content on the conversion.

TABLE 5

| WATER/PARA-HYDROXYBENZOIC ACID (MLS/GRAMS) | CONVERSION OF PARA-HYDROXYBENZOIC ACID (%) |
|---|---|
| 2 | 66 |
| 4 | 72 |
| 6 | 75 |
| 8 | 78 |

EXAMPLE 6

Solvent Effect 100 grams of para-hydroxybenzoic acid and 120 mls of triethylamine was added to various solvents. Then 325 mls of vinyl acetate was added, and the reaction was carried out until no noticeable change of conversion occurred. The effect of the solvents is shown in Table 6.

TABLE 6

| SOLVENT | SOLVENT/PARA-HYDROXYBENZOIC ACID (ML/GRAM) | REACTION TEMPERATURE (°C.) | CONVERSION (%) |
| --- | --- | --- | --- |
| WATER | 4 | 55 | 43 |
| DIMETHYLSULFOXIDE | 4 | 86 | 45 |
| N,N-DIMETHYLFORMAMIDE | 8 | 75 | 45 |

EXAMPLE 7

Effect of Unsubstituted Phenol, Mono-Substituted Phenols and Mono-Substituted Naphthol One mole each of four different phenols together with potassium hydroxide was added to water (weight 4 times that of the corresponding mono-substituted phenol). After adding 1.2 mole vinyl acetate the solution was reacted at 28° C. until no further change in conversion was noticed. The results are summarized in Table 7.

TABLE 7

| REACTANT | AMOUNT OF KOH (MOLE) | CONVERSION OF REACTANT (%) |
| --- | --- | --- |
| PHENOL | 0.27 | 36 |
| p-CHLOROPHENOL | 0.3 | 63.4 |
| p-HYDROXYBENZOIC ACID | 1.5 | 70 |
| m-HYDROXYPHENOL | 0.09 | 78 |
| 2-HYDROXY-6-NAPHTHOIC ACID | 1.5 | 67.1 |

Since many embodiments of this invention may be made and since many variations in the details disclosed are possible, the foregoing is to be interpreted as illustrative only, and the scope of our invention is set fourth in the following claims.

We claim:

1. A process for the acetylation of a mono-substituted phenol or a mono-substituted naphthol wherein the substituent in the mono-substituted phenol is selected from the group consisting of halo, hydroxy and carboxy at o, m, or p position with respect to the hydroxy group of phenol, and the mono-substituted naphthol is 2-hydroxy-naphthoic acid, said process comprising the steps of: reacting, as an acetylating agent, vinyl acetate at a temperature of not more than 160° C. with the said mono-substituted phenol or the said mono-substituted naphthol, which has previously been neutralized with a base to a salt and dissolved in a suitable solvent; separating the product from the reaction; and then purifying the separated product.

2. The process according to claim 1 wherein the reaction is carried out at temperature of from about 20° to 70° C.

3. The process according to claim 1 wherein the reaction is carried out at a pressure of from about 1 to 10 atmospheres.

4. The process according to claim 1 wherein vinyl acetate is present in an amount of from about 1 to 10 mole ratio based on the mono-substituted phenol or mono-substituted naphthol.

5. The process according to claim 1 wherein the base used is the hydroxide or the carbonate of lithium, sodium, potassium, or rubidium, or an organic amine, or ammonium hydroxide, and the molar ratio of the base to the mono-substituted phenol or mono-substituted naphthol is from 0.05 to 2.5.

6. The process according to claim 1 wherein the suitable solvent is water, dimethylsulfoxide, N,N-dimethylformamide, or N,N-dimethylacetamide.

7. The process according to claim 1, wherein the reaction is carried out at a pressure of from about 1 to 3 atmospheres.

* * * * *